US006703518B1

(12) United States Patent
Xu et al.

(10) Patent No.: US 6,703,518 B1
(45) Date of Patent: Mar. 9, 2004

(54) FLUORIDE-RELEASING COMPOSITIONS

(75) Inventors: Xiaoming Xu, Metairie, LA (US); John O. Burgess, New Orleans, LA (US); Xingzhe Ding, Aurora, CO (US); Long Ling, Metairie, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 10/382,800

(22) Filed: Mar. 5, 2003

(51) Int. Cl.[7] ............................. C07F 7/00; C07F 3/06; C07F 5/06; C07F 9/02; C07C 69/52
(52) U.S. Cl. ............................. 556/56; 556/13; 556/55; 556/105; 556/131; 556/133; 556/153; 558/70; 560/221; 562/571; 562/575; 534/15
(58) Field of Search ............................. 556/55, 56, 13, 556/105, 131, 133, 183; 560/221; 558/70; 562/571, 575; 534/15

(56) References Cited

U.S. PATENT DOCUMENTS

| 4,871,786 A | 10/1989 | Aasen et al. ................ 523/113 |
| 5,332,429 A | 7/1994 | Mitra et al. .................... 106/35 |
| 6,391,286 B1 | 5/2002 | Mitra et al. .................... 424/54 |

FOREIGN PATENT DOCUMENTS

WO       WO 00/69394       11/2000

OTHER PUBLICATIONS

Burgess, J. et al., "Novel Fluoride Releasing Dental Composite Resin," Research Grant Proposal submitted to Joe W. and Dorothy Dorsett Brown Foundation (1999).

Chikuma, M. et al., "Selective Sorption of Fluoride Ions by Anion–Exchange Resin Modified with Alizarin Fluorine Blue–Praseodymium (III) Complex," *Reactive Polymers*, vol. 13, pp. 131–138 (1990).

Ding, X. et al., "Effects of Silane Coupling Agents on the Fluoride Release from Experimental Dental Composite," Abst. #1970, p. A–255, *Journal of Dental Research*, vol. 81 (Special Issue A) (80th General Meeting of International Association for Dental Research, 31st Annual Meeting of the American Association of Dental Research, and 26th Annual Meeting of the Canadian Association for Dental Research, Mar. 6–9, 2002, San Diego, CA).

Ding, X. et al., "Mechanical Properties of Experimental Fluoride–Releasing Dental Composites," Paper #1316 to be presented at the 32nd Annual Meeting of the American Association of Dental Research and 27th Annual Meeting of the Canadian Association for Dental Research (Mar. 12–15, 2003, San Antonio, TX).

Glasspoole, E. et al., "A Fluoride–Releasing Composite for Dental Applications," *Dental Materials*, vol. 17, pp. 127–133 (2001).

Peutzfeldt, A., "Resin Composites in Dentistry: The Monomer Systems," *Eur. J. Oral. Sci.*, vol. 105, pp. 97–116 (1997).

Rawis, H. et al., "Esthetic Materials with Active Agent Control Release Capabilities and Their Future Roles," pp. 130–135 in *Symposium on Esthetic Restorative Materials*, 1991 (American Dental Association 1993).

Rawls, H., "Preventive Dental Materials: Sustained Delivery of Fluoride and Other Therapeutic Agents," Advances in Dental Research, vol. 5, pp. 50–55 (Dec. 1991).

Xu, X. et al., "Fluoride Release and Recharge of Experimental Dental Composites Containing Fluoride–Exchanging Metal Chelates," Paper #0936 to be presented at the 32nd Annual Meeting of the American Association of Dental Research and 27th Annual Meeting of the Canadian Association for Dental Research (Mar. 12–15, 2003, San Antonio, TX).

Yuchi, A. et al., "Complexes of Hard Metal Ions with Amine–N–Polycarboxylates as Fluoride Receptors," *Bull. Chem. Soc. Jpn.*, vol. 69, pp. 3173–3177 (1996).

Zimmerman et al., "Prevention of in vitro Secondary Caries with an Experimental Fluoride–Exchanging Restorative Resin," *J. Dental Res.*, vol. 63, pp. 689–692 (1984).

*Primary Examiner*—Porfirio Nazario-Gonzalez
(74) *Attorney, Agent, or Firm*—John H. Runnels

(57) ABSTRACT

Chelating monomers and fluoride-releasing compositions are disclosed that may be incorporated into dental composite restorative materials or other dental materials, to produce materials with high fluoride release rates, and high fluoride recharge capability. Such resins may be used in dental restorative materials to help reduce the level of dental caries in patients, particularly the level of caries occurring on the margins of the restorative materials.

6 Claims, No Drawings

FLUORIDE-RELEASING COMPOSITIONS

This invention pertains to compositions useful in dental composites or in other composite materials, particularly to compositions that release fluoride ion and that may be recharged with additional fluoride ion.

Fluoride is the most widely used agent to prevent dental caries (tooth decay). Tooth decay can occur on the margins of dental restorations. Such recurring caries is a frequent cause for failure of dental restorations. Fluoride-releasing restorative materials have been used to try to reduce recurrent caries at restoration margins. The effectiveness of such fluoride-releasing materials varies widely. Fluoride-releasing materials generally fall into one of four categories: glass ionomers, resin-modified glass ionomers, compomers, and fluoride-releasing composite resins. In general, materials with higher levels of fluoride release tend to have poorer mechanical properties (e.g., a lower compressive strength) High fluoride-releasing materials have therefore been used clinically primarily to restore decayed, but non-biting areas.

Glass ionomers and resin-modified glass ionomers release fluoride as a by-product during acid-base reactions between the ion-leachable fluoride glass and an acidic liquid. Glass ionomers and resin-modified glass ionomers generally have high fluoride release and recharge capabilities, but they have low strength and poor esthetic qualities. Composite resins have been widely used in restorative dentistry because they have high strength, good wear resistance, and excellent esthetics, but they release relatively small amounts of fluoride, and have low fluoride-recharge capabilities. There is an unfilled need for dental composite resins with high strength, good wear resistance, high fluoride release rates, and high fluoride recharge capability.

Currently, fluoride released from resin-based dental restorative materials comes from four main sources: (1) a soluble free salt, such as NaF, KF, or $SnF_2$ added to the material; (2) fluoride-releasing glass fillers such as fluoroaluminosilicate glass or sparingly soluble inorganic salts such as $YbF_3$; (3) polymer molecules containing an anion-exchangeable fluoride moiety such as $—N(CH_3)_2HF$; (4) or organic fluoride sources such as those from alkylonium tetrafluoroborate.

U.S. Pat. No. 6,391,286 discloses fluoride releasing materials for use in dental compositions, having the formula $M(G)_g(F)_n$ or $M(G)_g(ZF_m)_n$, where M is an element capable of forming a cationic species and having a valence of 2 or more; G is an organic chelating moiety capable of complexing with the element M; Z is hydrogen, boron, nitrogen, phosphorus, sulfur, antimony, or arsenic; F is fluoride; and g, m, and n are at least 1.

U.S. Pat. No. 4,871,786 discloses dental compositions employing one or more substantially soluble organic compounds that serve as fluoride sources by incorporating tetrafluoroborate. Preferred non-polymerizable fluoride sources were said to be compounds of the formula: $R_n—M^+$ $BF_4^-$ where M is I, N, P, or S; n is 2, 3, or 4, depending on the identity of M; and R is one of several specified types of substituted or unsubstituted hydrocarbon chains. Preferred polymerizable fluoride sources were said to be compounds of the formula: $R_{(n-1)}—M^+(L) BF_4^-$ where the other symbols were as previous stated, and L is an organic ligand comprising a moiety capable of polymerization via a cationic, condensation, or free radical mechanism.

Published international patent application WO 00/69394 discloses what were said to be stable one-part dental materials comprising a compound having only one acid functionality and at least one polymerizable functionality on each compound. The material does not contain storage-deleterious quantities of polyacid compounds. The material also contains a fluoride source containing polyvalent metal ions, and a photopolymerization initiator.

A Yuchi et al., "Complexes of Hard Metal Ions with Amine-N-Polycarboxylates as Fluoride Receptors," *Bull. Chem. Soc. Jpn.*, vol. 69, pp. 3173–3177 (1996) discloses studies of equilibria in the reaction of hard metal complexes $(M^{m+}: Al^{3+}, Zr^{4+}, Hf^{4+}, Th^{4+}; H_nL:$ amine-N-polycarboxylic acid) with fluoride. The zirconium (IV) complex of N-methyliminodiacetic acid was reported to be an excellent fluoride receptor.

M. Chikuma et al., "Selective Sorption of Fluoride Ions by Anion-Exchange Resin Modified with Alizarin Fluorine Blue-Praseodymium (III) Complex," *Reactive Polymers*, vol. 13, pp. 131–138 (1990) disclosed a resin for the selective sorption of fluoride ion, prepared from an anion exchange resin, Amberlite IRA 400, and a praseodymium (III) complex of alizarin fluorine blue.

H. Rawls et al., "Esthetic Materials with Active Agent Control Release Capabilities and Their Future Roles," pp. 130–135 in *Symposium on Esthetic Restorative Materials*, 1991 (American Dental Association 1993) provides a review of dual-purpose dental restorative materials: those that can serve the needs of esthetic dentistry and that can also serve as sustained-release sources of therapeutic agents, such as fluoride. See also H. Rawls, "Preventive Dental Materials: Sustained Delivery of Fluoride and Other Therapeutic Agents," *Advances in Dental Research*, vol. 5, pp. 50–55 (December 1991).

A. Peutzfeldt, "Resin Composites in Dentistry: The Monomer Systems," *Eur. J. Oral Sci.*, vol. 105, pp. 97–116 (1997) provides a general review of dental resin monomers and composites, including some that release fluoride.

E. Glasspoole et al., "A Fluoride-Releasing Composite for Dental Applications," *Dental Materials*, vol.17, pp. 127–133 (2001) discloses the incorporation of an organic fluoride material, tetrabutylammonium tetrafluoroborate, into a hydrophilic monomer system made of 2,2-bis[4-(2-hydroxy-3-methacroyloxypropoxy)phenyl]-propane and 2-hydroxyethyl methacrylate. Resulting fluoride release rates were reported to exceed those of several glass ionomer materials that were also tested.

B. Zimmeran et al., "Prevention of in vitro Secondary Caries with an Experimental Fluoride-Exchanging Restorative Resin," *J. Dental Res.*, vol.63, pp. 689–692 (1984) reported clinical observations in which experimental composite resins that released fluoride by ion exchange were seen to reduce the incidence of caries in immediately adjacent areas, as compared to the rates of caries observed when non-fluoride-containing materials were used.

We have discovered novel fluoride-releasing compositions that may be incorporated into dental composite restorative materials or other dental materials, to produce materials with high fluoride release rates and high fluoride recharge capability. Such resins may be used, for example, in dental restorative materials to help reduce the level of dental caries in patients, particularly the level of caries occurring on the margins of the restorative materials.

The novel chelating and fluoride-releasing monomers may be described by the following general formulas, where the first formula below depicts a chelating monomer, and the second depicts the monomer chelated to a metal atom, which in turn is coordinated to one or more fluoride ions:

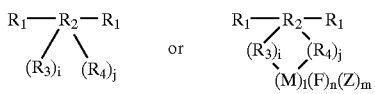

where $R_1$ is a substituted or unsubstituted aliphatic or aromatic group having 2 to 24 carbon atoms, and having at least one polymerizable group, the polymerizable group being preferably, but not necessarily, located in a terminal position; $R_2$ is a substituted or unsubstituted aliphatic or aromatic group having 2 to 50 carbon atoms; M is a metal atom having a valence of +2 or higher; $R_3$ and $R_4$ are unidentate or multidentate ligands that can form a coordination bond or ionic bond with M; $R_3$ and $R_4$ can be the same or different, but at least one them is a multidentate (at least a bidentate) ligand; i, j, l, and n are positive integers; F is a fluoride atom; Z is a counter-ion to maintain the neutrality of the monomer; and m is an integer from 0 to 4.

One advantage of having two coordinating ligands, $R_3$ and $R_4$, is that the combination forms a more stable chelate with the metal, which can help minimize the loss of metal ion from the material under conditions of use.

Preferred embodiments of the invention include one or more of the following options: (1) the use of multiple polymerizable terminal groups in the $R_1$ moieties, such as di- or polymethacrylates, to form a cross-linked polymer matrix with better mechanical properties and lower monomer loss than typically occurs with metallofluorocomplexes containing one or zero polymerizable groups; (2) adjusting the spatial arrangement of $R_3$ and $R_4$ by, for example, changing the length of one of the ligands to optimize formation of the fluoride-metal chelate and the later release of fluoride from the chelate; (3) multinucleate metal chelates (i.e., a single monomer structure containing more than one metal atom), which can increase the fluoride release and recharge capability.

This invention provides a class of polymerizable monomers containing chelating groups and fluoride-exchanging metal chelates that can release fluoride into an aqueous solution, and that can "recharge" by taking up fluoride from an aqueous solution containing a high concentration of fluoride (e.g., a fluoridated toothpaste or mouthwash).

In the general formula above, M is a metal having a valence of +2 or greater. Preferred metals M are those having +3 or +4 valences, particularly those that tend to form colorless complexes with the ligands and with fluoride. For example, M may be $Sn^{+2}$; $Zn^{+2}$, $Sr^{+2}$, $Al^{+3}$, $La^{+3}$, $Ce^{+3}$, $Sb^{+3}$, $Yb^{+3}$, $Ti^{+4}$, $Sn^{+4}$, $Zr^{+4}$, $Ce^{30\ 4}$, or $Th^{+4}$. Particularly preferred is $Zr^{+4}$, because that cation is nontoxic, colorless, relatively inexpensive, has a high valence, and has a high tendency to form multinucleate complexes with fluoride ions, leading to high fluoride-exchange capacity. In addition, Zr has a high atomic weight, providing radiopacity, a desirable property for dental restorative materials. Z is a counter ion to maintain the neutrality of the monomer, for example hydrogen, lithium, sodium, potassium, ammonium or quaternary ammonium. Preferred Z include hydrogen or sodium.

The $R_1$ group contains at least one polymerizable moiety such as a C=C double bond, an expoxy group, an ethyleneimine group, etc. Preferred $R_1$ groups include the esters of acrylic or methacrylic acid. Specific examples include methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate, hydroxypropyl acrylate, hydroxypropyl methacrylate, tetrahydrofurfuryl acrylate, tetrahydrofurfuryl methacrylate, glycidyl acrylate, glycidyl methacrylate, glycerol mono- and di-acrylate, glycerol mono- and di-methacrylate, ethyleneglycol diacrylate, ethyleneglycol dimethacrylate, neopentyl glycol diacrylate, neopentylglycol dimethacrylate, and trimethylolpropane triacrylate.

Other suitable examples of $R_1$ include vinyl azalactone, vinyl pyrrolidone, styrene, divinylbenzene, urethane acrylates or methacrylates, epoxy acrylates or methacrylates and polyol acrylates or methacrylates, substituted acryl amides and methacrylamides.

Alternatively, the polymerizable component may be a cationically curable material, such as one of the epoxies, oxetanes, oxolanes, cyclic acetals, lactams, lactones, vinyl ethers, and spirocyclic compounds containing one or more oxygen atoms in the ring.

$R_2$ is a substituted or unsubstituted aliphatic or aromatic group containing 2 to 50 carbon atoms. The structure of $R_2$ should permit the bonding of at least four functional groups (two $R_1$, an $R_3$, and an $R_4$). Preferred $R_2$ groups are derivatives of aromatic diols, diacids, and diepoxides, such as substituted or unsubstituted bisphenols, hydroquinone, diphenols, and dihydroxyphthalic acid. Other suitable examples for $R_2$ include aliphatic diamines such as polyethylenediamines and polyethyleneglycodiamines, and derivatives of citric acid, tartaric acid, cyclohexane, cyclopentane, tetrahydrofuran, and tetrahydropyrrole. The structures of preferred $R_2$ groups are illustrated by the general formulas:

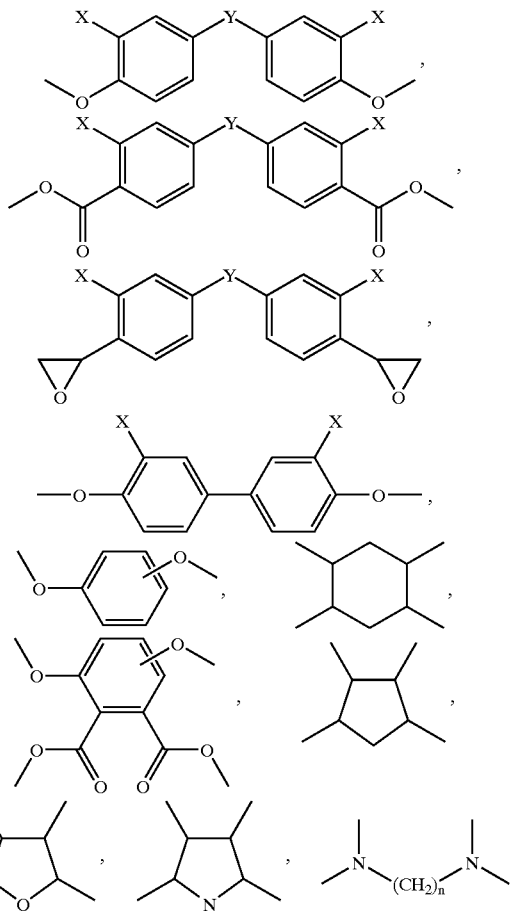

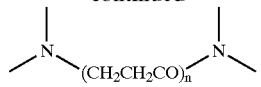

where X is hydrogen or a substituted or unsubstituted alkyl group having from 1 to 12 carbon atoms, such as methyl, ethyl, propyl, isopropyl, butyl, or t-butyl. Y is $C(CH_3)_2$, $CH_2$, O, CO, S, $SO_2$, or $CH_3CCH_2COOH$. The value of n is an integer from 1 to 12.

$R_3$ and $R_4$ are unidentate or multidentate ligands that can form coordination bonds or ionic bonds with M. $R_3$ and $R_4$ are covalently bonded to $R_2$. $R_3$ and $R_4$ can be the same or different, but at least one of them should be at least a bidentate or multidentate ligand capable of forming a 4–8 member ring when chelating the metal ion M. Preferred structures for $R_3$ and $R_4$ have a combined ligand number of 3 or 4 (not counting the bonds to the fluoride, or the coordination bonds formed by the lone electron pairs from N, O, S, etc.).

A wide variety of ligands may be used for $R_3$ and $R_4$. Examples of multidentate ligands include substituted carboxylic di-acids or tri-acids and their salts, such as aminodiacetic acid, amidodiacetic acid, benzyliminodiacetic acid, phthalic acid, salicylic acid, citric acid, tartaric acid, hydroxamic acid, cyclohexen-1,2-diacid, phosphoric acid, aminophosphoric acid, phosphonic acid, and 8-hydroyquinoline. Examples of unidentate ligands include compounds with a hydroxyl group, such as alcohols; carboxylic acids; and a half ester (derived from an anhydride or chloride) of an aliphatic or aromatic diacid having from 2 to 12 carbon atoms, such as oxalic acid, malonic acid, maleic acid, a disubstituted maleic acid, succinic acid, fumaric acid, malic acid, tartaric acid, glutaric acid, glutaconic acid, adipic acid, pimelic acid, cyclohexen-1,2-diacid, (o, m, or p)-phthalic acid, citric acid, hydroxyphthalic acid, suberic acid, trimellitic acid, sebaric acid, and their salts.

Particularly preferred chelating monomers are compounds containing aminodiacetic acid, amidodiacetic acid, phosphonic acid, or aminophosphoric acid groups, and having a molecular weight between 100 and 2000, for example, one of the following structures M1 to M20:

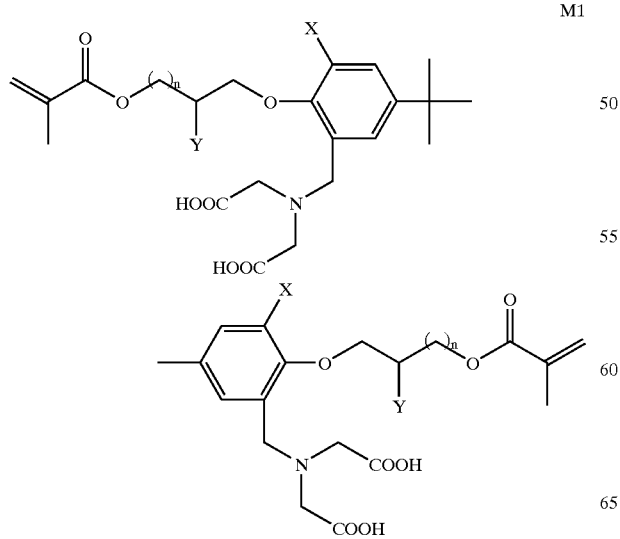

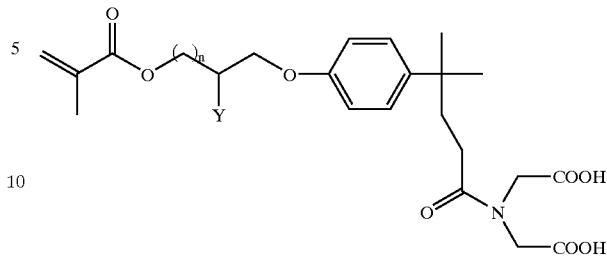

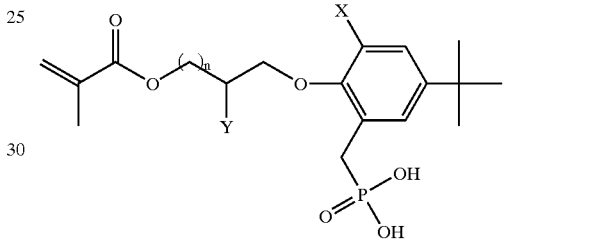

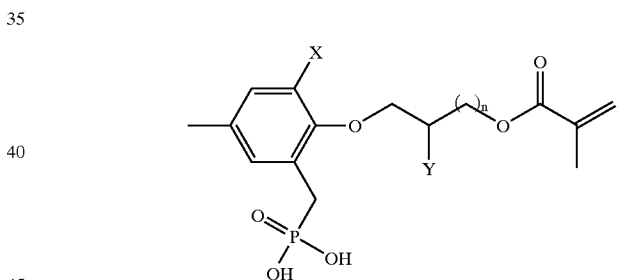

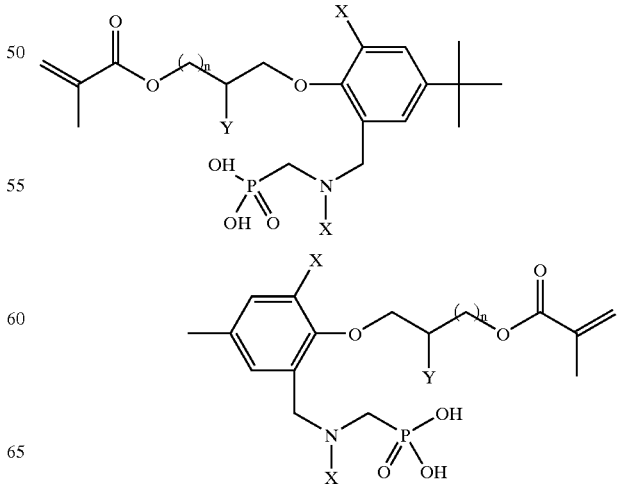

-continued
M5
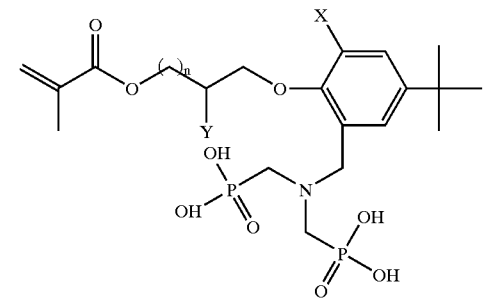
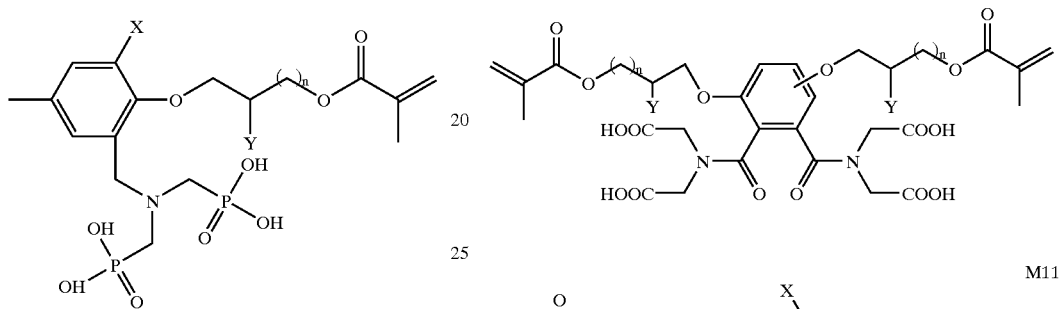
M6
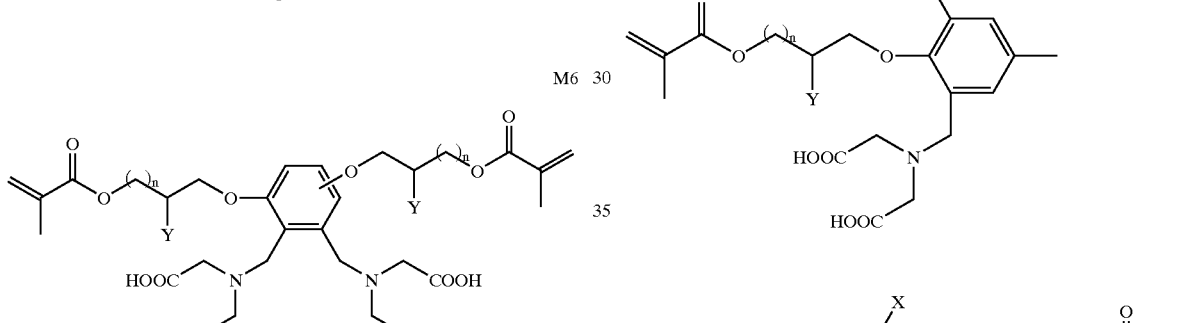
M7
-continued
M9
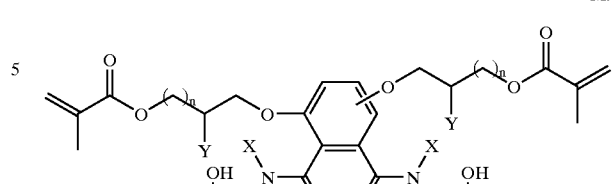
M10
M11
M12
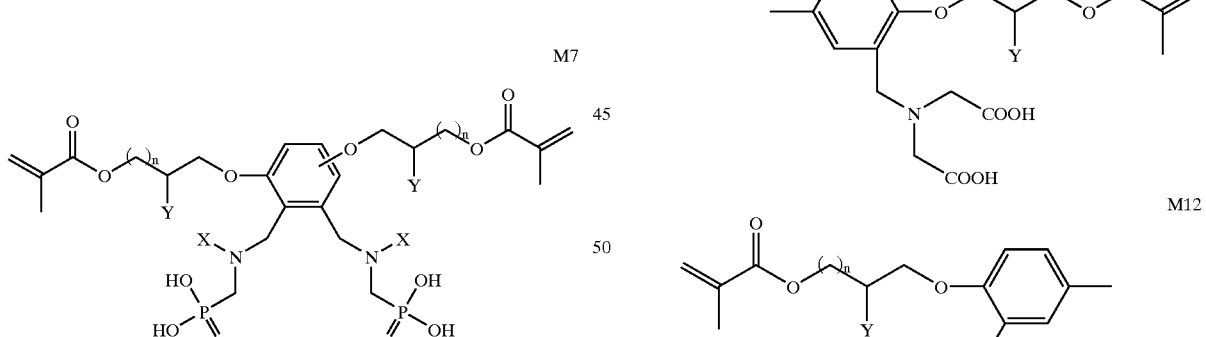
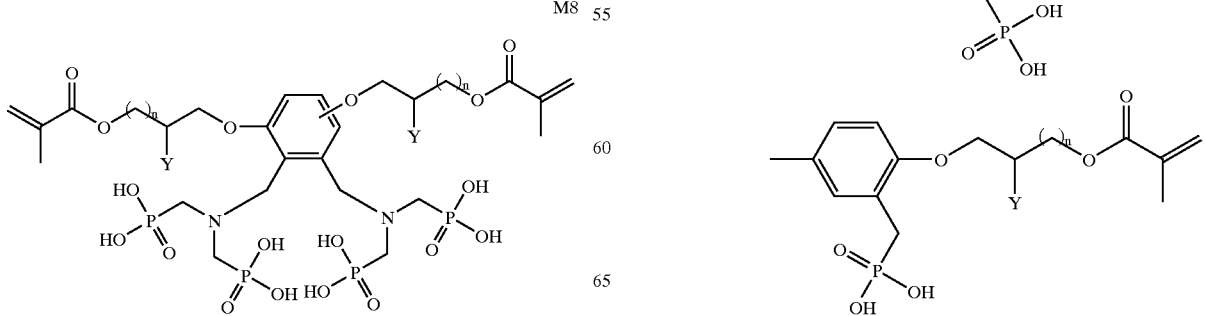
M8

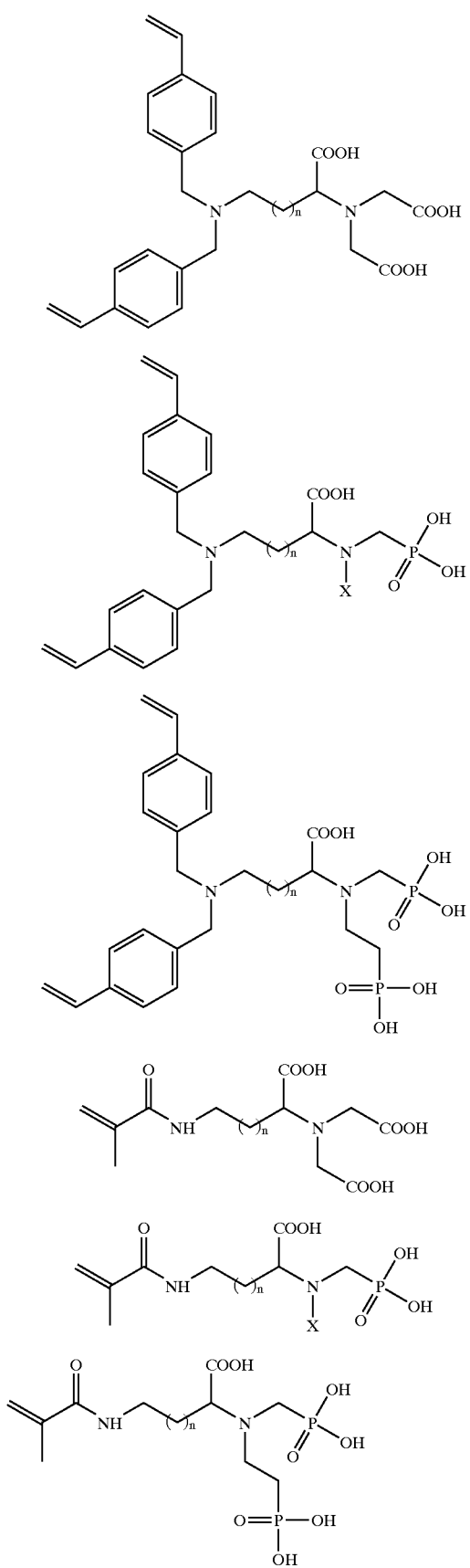

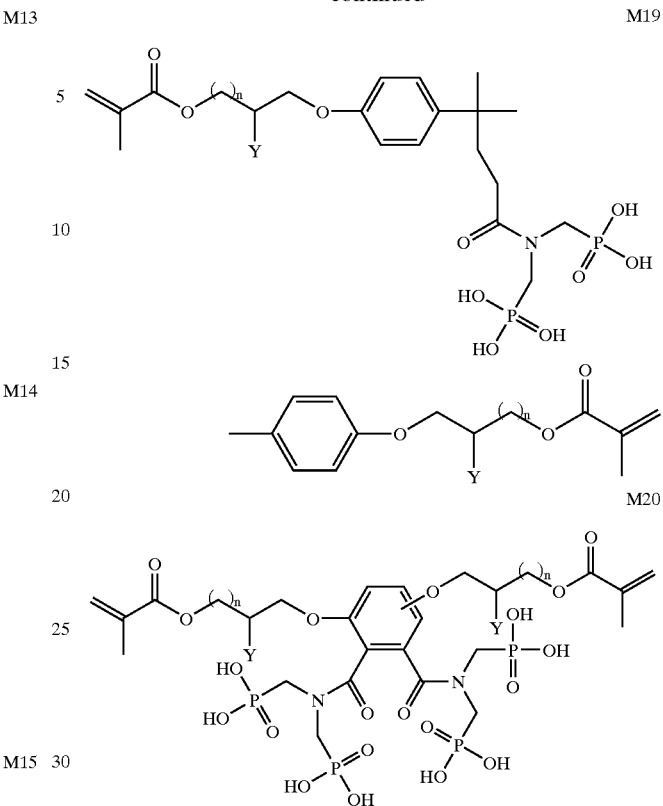

where X is hydrogen, or a substituted or unsubstituted alkyl group having from 1 to 12 carbon atoms such as methyl, ethyl, propyl, isopropyl, butyl, or t-butyl. Using an alkyl group as X will help reduce the hydrophilicity of the monomer, and can help inhibit unwanted substitution reactions. Y is a pendent group that may or may not participate in chelate formation. The simplest Y is hydrogen, which does not participate in chelate formation; and a typical Y is a hydroxyl group, which can participate in chelation. Y may also be, for example, an ester of a phosphoric acid, or a half ester of an aliphatic or aromatic diacid or triacid having from 2 to 12 carbon atoms, such as oxalic acid, malonic acid, maleic acid, a disubstituted maleic acid, malic acid, succinic acid, fumaric acid, malic acid, tartaric acid, glutaric acid, glutaconic acid, citric acid, adipic acid, pimelic acid, cyclohexen-1,2 diacid, (o, m, or p)-phthalic acid, hydroxyphthalic acid, suberic acid, trimellitic acid, or sebaric acid. The chain length of such a diacid or triacid may be selected to optimize the formation of the fluoride-exchange metal chelate and the release of fluoride thereof. The various X groups depicted in the above structures may be the same as, or different from one another, as may the various Y groups. The number n is an integer from 0 to 12.

Following are preferred synthetic schemes for synthesizing the preferred monomers for use in the present invention (1) Add a chelating ligand to $R_2$ which is an aromatic diol, such as a substituted or unsubstituted bisphenol, diphenol, or hydroquinone.

(a) Iminodiacetic acid undergoes a Mannich-type reaction with $R_2$ and formaldehyde or polyformaldehyde in an aprotic polar solvent such as DMF or dioxane at 80° C. for several hours to overnight. This process generates precursors for monomers such as M1, M6, and M11, where Y is not hydrogen and n is at least 1.

(b) For a precursor to M1, diethyl iminodiacetate may be used instead, followed by reaction with bromoethanol or ethylene carbonate to add —O($CH_2$)$_2$OH groups, then hydrolysis with $K_2CO_3$/NaOH, and acidifying with HCl.

(c) To add aminophosphoric groups (e.g., M4, M5, M7, and M8), $R_2$ first undergoes a Mannich-type reaction with $CH_2O$ and $NH_3$, then reacts with $CH_2O$ and $PCl_3$ or HP(O)(OCH$_2$CH$_3$)$_2$, followed by hydrolysis. For monomers M4, M7, M9, M14 and M17, the amount of $PCl_3$ or diethyl phosphite should be controlled so that only one phosphite group attaches to the amine. Then the secondary amine may be converted into a tertiary amine through an Eichweich-Clark reaction, i.e. reduction by formic acid in the presence of formaldehyde (X=$CH_3$).

(d) To add chelating groups to $R_2$ through amide groups (e.g., M2, M9, M10, M19, and M20), the carboxylic acids on $R_2$ first react with iminodiacetic acetate (for M2 and M10) or $NH_3$ (for M9, M19, and M20) in 1,4-dioxane in the presence of 1-methyl-2-chloropyridiniumiodide and triethylamine at room temperature, followed by hydrolysis with $K_2CO_3$/NaOH, and acidifying with HCl to yield precursors of M2 and M10, or reaction with $CH_2O$ and $PCl_3$ to yield a precursor of M9.

(e) To add phosphonic acid groups (e.g., M3 and M12), 3,3'-dimethyl-bisphenol A or diphenol is first reacted with bromoethanol or ethylene carbonate to add —O($CH_2$)$_2$OH groups; and then reacted with pyridinium tribromide (CH$_5$NH)Br$_3$ to convert the methyl group to —$CH_2$Br, which further reacts with P(OCH$_3$)$_3$ or (POCH$_2$CH$_3$)$_3$ to form a methyl phosphonate, which can later be hydrolyzed to a phosphonic acid with trimethylsilyl bromide and a methanol/water mixture.

(2) Add a polymerizable terminal group $R_1$ (e.g., a methacrylate).

(a) The above precursors with chelating groups will react with 2,3-epoxypropyl methacrylate or 2,3-epoxyalkyl methacrylate (alkyl containing 3 to 12 carbon atoms) in 1,4-dioxane at 100° C. for 24 hours to add a hydroxypropyl methacrylate or hydroxyalkyl methacrylate to each phenol group (Y=OH). Monomers M1 to M12, M19, and M20 may be prepared in this way from the precursors generated in step (1).

(b) For the special case where Y is a hydrogen (i.e., no pendent Y group), a methyl or ethyl ester of the chelating group (e.g., iminodiacetic acid or phosphoric acid) may be used in step (1). Then the resulting precursors may react first with bromoalcohol or ethylene carbonate (n=0) to add ($CH_2$)$_{n+2}$OH (n=0 to 12), followed by hydrolysis to convert the esters of the chelating groups to the acids. Then the resulting products react with methacryloyl chloride in DMF or 1,4-dioxane.

(3) M13 to M18 may be prepared as follows: first, the sterically less hindered amino group of (D,L)-lysine is selectively acrylated by reaction with benzyl cyanoformate, followed by reaction with bromoacetic acid (for M13 and M16) or $PCl_3$, followed by hydrolysis (for M14, M15, M17, and M18). Removal of the benzyl protecting group will proceed in high yield by hydrogenolysis. The product further reacts with 1-chloromethyl-4-vinylbenzene to yield M13, M14, and M15; or with methacryloyl chloride to yield M16, M17, and M18.

(4) The pendent hydroxyl group (Y) may be converted to a stronger ligand, such as a phosphoric acid ester, or a half ester of an aliphatic or aromatic diacid or triacid having from 2 to 12 carbon atoms, by reaction with the corresponding anhydrides or chlorides followed by hydrolysis. Specific examples of such diacids or triacids include oxalic acid, malonic acid, maleic acid, disubstituted maleic acid, malic acid, succinic acid, fumaric acid, malic acid, tartaric acid, glutaric acid, glutaconic acid, tartaric acid, citric acid, adipic acid, pimelic acid, cyclohexen-1,2 diacid, (o, m, or p)-phthalic acid, suberic acid, trimellitic acid, and sebaric acid. The chain length of the diacid may be selected to optimize formation of the fluoride-exchanging metal chelate, and the release of fluoride from the chelate.

The preferred fluoride-releasing monomers may be prepared from chelating monomers such as those described above and metal fluorides. Methods of preparation include the following three:

(1) The acidic chelating monomers are reacted directly with a metal fluoride in a polar organic solvent such as methanol, DMF, or tetraethyleneglycol dimethacrylate. This process is easy to carry out, but can be slow (e.g., 1 to 7 days), unless the metal fluoride has substantial solubility in the solvent.

(2) The acidic chelating monomers are first reacted with metal salts that are partially soluble in the organic solvent, e.g., nitrates or acetates, and then fluoride is added, e.g., as. HF, NaF, NH$_4$F, LiF, or a tetraalkyl ammonium fluoride such as (CH$_3$)$_4$NF, (C$_2$H$_5$)$_4$NF, or [CH$_3$(CH$_2$)$_3$]$_4$HF.

(3) First, a metal fluoride salt, e.g., ZrF$_4$, is dissolved in concentrated hydrofluoric acid (HF) or a mixture of HF with a fluoride salt such as NaF, NH$_4$F, LiF, [CH$_3$(CH$_2$)$_3$]$_4$NF, etc. The resulting solution containing metal-fluoride complexes, such as [ZrF$_5$]$^-$ or [Zr$_2$F$_9$]$^-$, then reacts with the monomer-methanol solution. This reaction is fast at room temperature, and is therefore is the most efficient of the three methods; but it is only useful for those metals (e.g., Zr, Al) that form anionic fluoride complexes that are soluble in water and methanol. The excess HF and unreacted metal-fluoride complexes can be removed by evaporation and absorption with Ca(OH)$_2$, followed by redissolving the product in an organic solvent, such as isopropanol, in which Zr—F complexes will precipitate.

Some examples of fluoride-releasing monomers formed using such chelating monomers, zirconium, and fluoride are shown in the following structures:

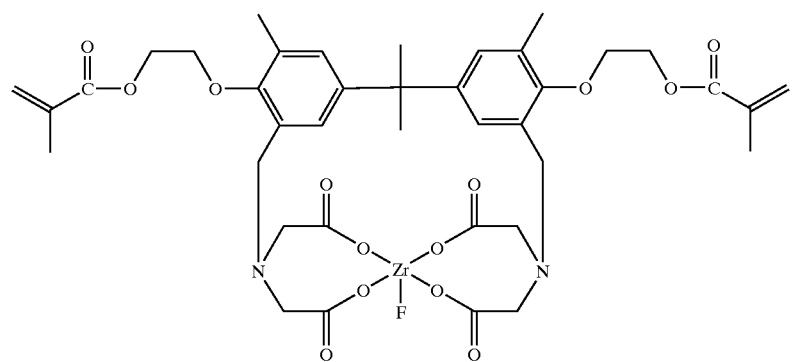
M1-ZrF
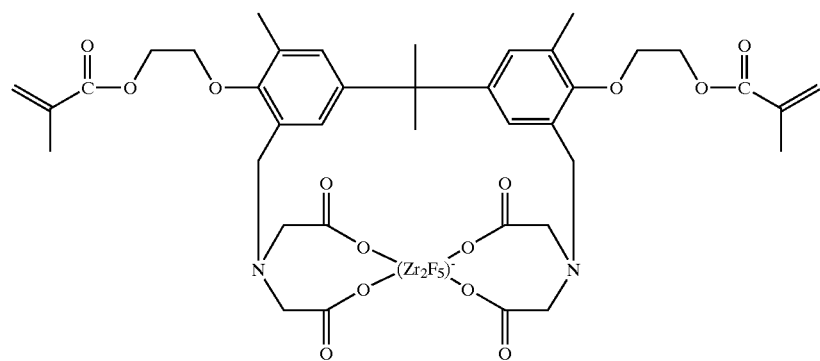
M1-Zr₂F₅
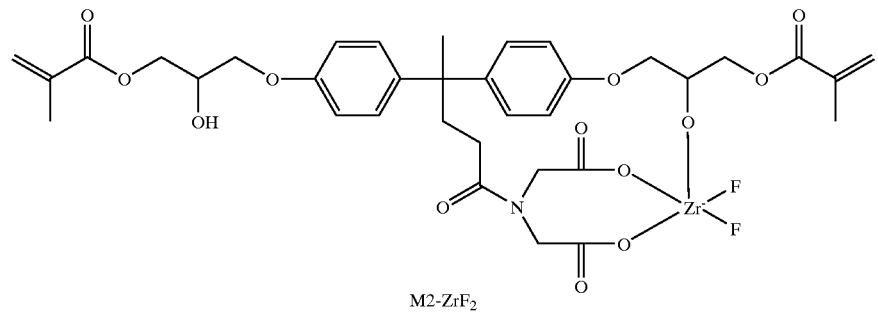
M2-ZrF₂
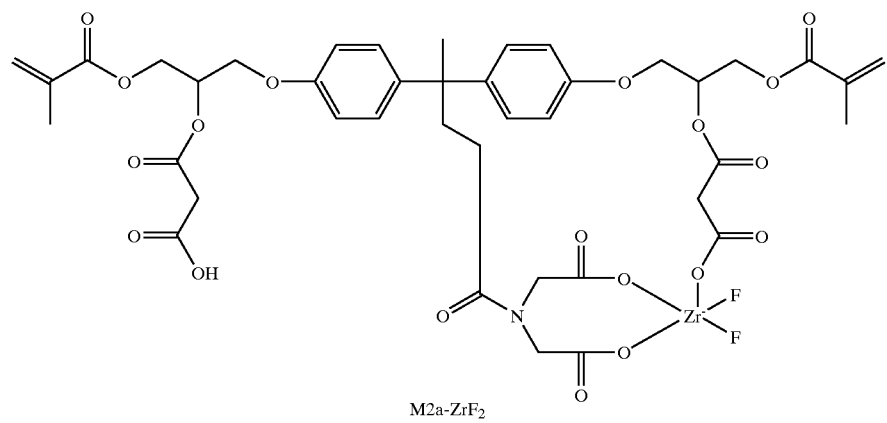
M2a-ZrF₂

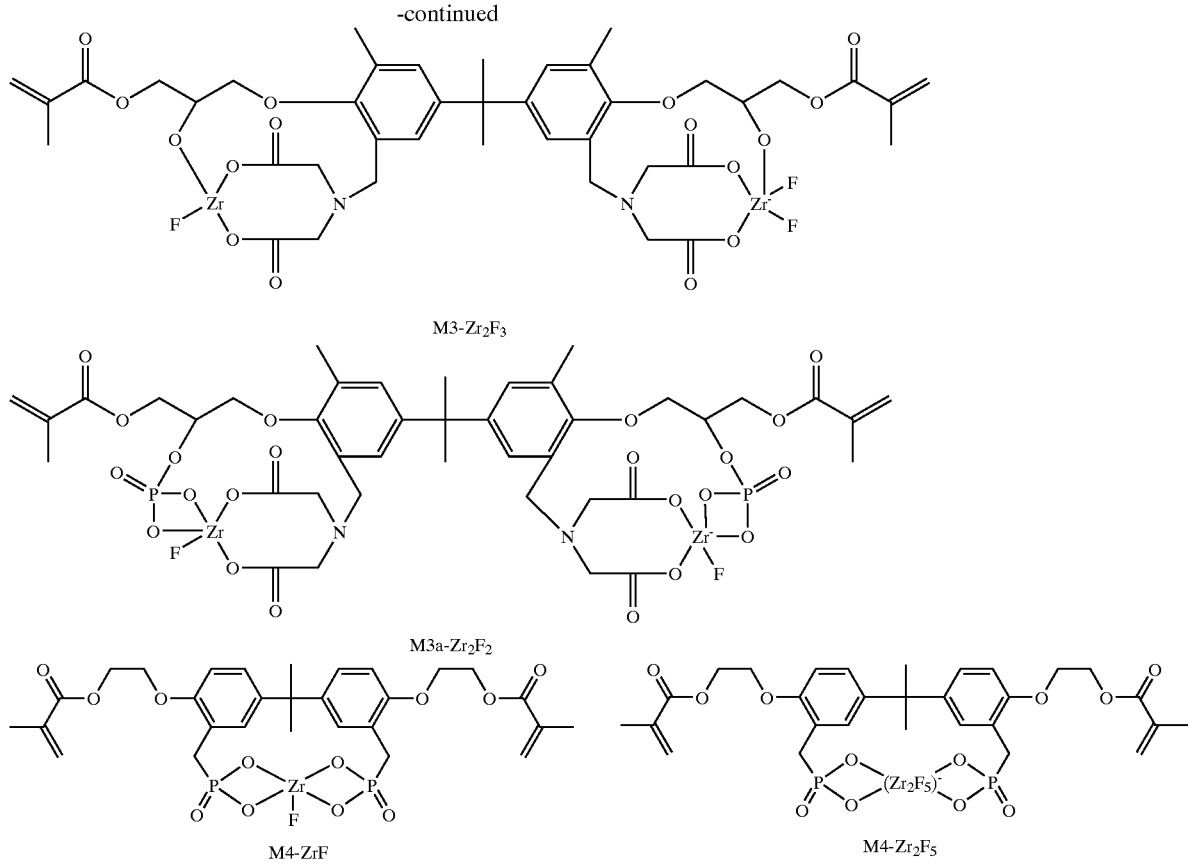

M3-Zr₂F₃

M3a-Zr₂F₂

M4-ZrF

M4-Zr₂F₅

The chelating monomers and fluoride-releasing monomers may be dissolved in, or mixed with, monomers or mixtures of monomers known in the art for use in dental materials, such as bisphenol A glycidyl dimethacrylate, hydroxyl ethyl methacrylate, triethyleneglycol dimethacrylate, and urethane dimethacrylate. The amount of the fluoride-releasing monomers may be from about 0.1% to about 70% by weight of total monomers, depending on the requirements for fluoride release and other physical and mechanical properties, the preferred ratio being from about 20% to about 40%. The monomer mixtures may be polymerized (cured) by means known in the art, such as free radical reactions initiated by photoinitiators or chemical initiators. Such photoinitiators include diketones such as camphorquinone, and 1-phenyl-1,2-propanedione (PPD). Chemical initiators are usually organic peroxides such as benzoyl peroxide. Reducing agents or accelerators may also be added, such as aliphatic or aromatic tertiary amines, for example dimethylaminoethyl methacrylate. The total ratio of initiators and accelerators is typically between about 0.03% and about 5% by weight of total materials, with a preferred range between about 0.3% and about 1%.

The chelating monomer, fluoride-releasing monomers and their mixtures with other monomers may be used with or without fillers. Preferred compositions for dental composite resins contain both fluoride-releasing monomers and fluoride-releasing filler particles such as a fluoroaluminosilicate glass, for example, that described in U.S. Pat. No. 5,332,429. The fillers may also include other inorganic compounds such as $SiO_2$, $ZrO_2$, $TiO_2$, $ZrF_4$, NaF, $AlF_3$, LiF, $SrF_2$, $CeF_3$, $Ca_3(PO_4)_2$, $La_2O_3$, $Ce_2O_3$ and glasses incorporating these compounds. Preferred particle sizes for fillers are 0.1 to 5 micrometer, more preferably 0.2 to 3 micrometer.

To enhance bonding between the filler and the resin matrix, the filler surface is preferably treated with a silane coupling agent, such as γ-methacryloyloxypropyltrimethoxysilane, γ-mercaptopropyltriethoxysilane, γ-aminopropyltrimethoxysilane, and O-(methacryloxyethyl)-N-(triethoxysilylpropyl)urethane. Alternatively, the filler particles may be treated with an organic acid containing polymerizable functional groups, including for example the chelating monomers of the present invention. The filler load varies by type of application: for example, it can range from about 5% to about 50% in a sealant or a filled dental adhesive, from about 40% to about 60% for flowable composites, and up to about 85% for posterior composites.

Applications for the chelating monomers and fluoride-releasing monomers of the present invention include, for example, dental restorative materials such as composite resins, compomers, resin-modified glass ionomers, sealant, liners, cements, provisional/temporary materials, dental adhesives (bonding agents), denture base resins, and orthodontic adhesives.

Alternatively, polymers and composites made from the novel chelating monomers and their metal chelates may also be used in the preparation of ion exchange resins, which may be used, for example, in the separation of metals, fluoride ions, and other anions by chemical manufacturers or analytical laboratories; or in the removal of hazardous metals or unwanted fluoride from industrial waste water. The chelating monomers may also be used to coat metal surfaces including dental and medical implants to enhance protection or bonding.

The following examples are presented to demonstrate the synthesis, fabrication, and testing of materials in accordance with the present invention. These examples are not intended to limit the scope of the invention in any way. All starting materials are commercially available (most of them from Sigma-Aldrich). IR spectra were recorded on a Bio-Rad FTS-40 FT-IR spectrometer. NMR spectra were measured on an Inova-500 ($^1$H & $^{13}$C) NMR spectrometer, $^1$H at 500 MHz, $^{13}$C at 125 MHz, using TMS as an internal standard. The F$^{19}$ NMR chemical shift was expressed relative to the position of the trifluoride toluene signal as 33.858 ppm. Electrospray mass spectrometry (ES-MS) was carried out on a Bruker Daltonics Esquire 3000 Ion Trap Electrospray Mass Spectrometer. In the formulas given for the assignment of mass spectra peaks, such as [M–4H+Zr+F]$^-$, M is the mass of the chelating monomer or its precursor; H, Zr, F are the mass of the most abundant isotope of hydrogen, zirconium, and fluorine, respectively. (I.e., H=1.00, Zr=89.90, F=19.00.) Zirconium has a unique isotope distribution (Zr$^{90}$ 51.45%, Zr$^{91}$ 11.27%, Zr$^{92}$ 17.17%, Zr$^{94}$ 17.37%, Zr$^{96}$ 2.78%), which can be used to identify its presence and abundance in a chelate. Note that some syntheses were run in more than one batch, although only one batch is reported below; hence the starting amount of a particular compound in a later synthetic step may sometimes appear to be more than was synthesized in an earlier step.

EXAMPLE 1

Synthesis of 2,2'-bis(4-hydroxy-3-methyl-5-methylamine-N,N,'-diethyl diacetate-phenyl)propane (Compound 1)

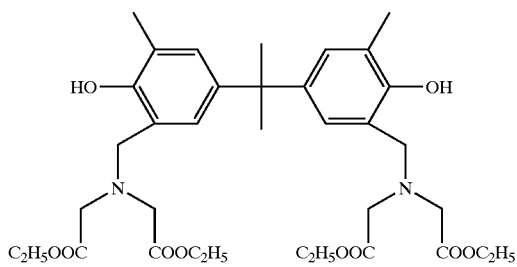

Compound 1

2,2'-Bis(4-hydroxy-3-methyl-phenyl)propane (12.81 g, 0.05 mol), diethyl iminodiacetate (22.70 g, 0.12 mol), and 100 ml ethyl alcohol were added to a 250 ml three-neck flask. The reactor contents were heated to a slight reflux, and then 37% formaldehyde (16.1 g, 0.2 mol) was added dropwise over a period of 8 hours. The reaction mixture was then stirred at 80° C. for another 8 hours. After that, it was concentrated to approximately 50 ml in an evaporator. 200 ml methanol was added at room temperature, and a fine, white powder precipitated. The solid was then recrystallized from methanol two times to obtain white crystalline Compound 1, 25.50 g (77.5% yield). Analysis: ES-MS (in MeOH): 657.2 ([M–H]$^-$, calculated: 657.35)

EXAMPLE 2

Synthesis of 2,2'-bis(4-hydroxyethoxy-3-methyl-5-methylamine-N,N'-diacetic acid-phenyl)propane (Compound 2)

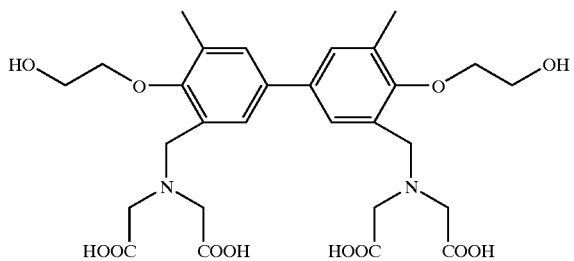

Compound 2

A three-neck flask was charged with Compound 1 (19.75 g, 0.03 mol), 200 ml of dry N,N-dimethyl formamide (DMF), and ethylene carbonate (17.6 g, 0.2 mol). After stirring and heating for 6 hours at 160° C., most of the solvent and un-reacted ethylene carbonate had evaporated. 150 ml methanol, 20 g potassium carbonate, and 100 ml water were added, and the mixture was heated to reflux for 12 hours. After removal of the solvent, 100 ml MeOH was added to the mixture, which was then filtered. 10% HCl was added to the solution to pH=2.0, and the mixture was then stirred overnight at room temperature. The precipitated solid was filtered, and the solvent was removed. The precipitate was redissolved in 50 ml MeOH, and was then purified from a silica gel column using CH$_2$Cl$_2$ with a MeOH gradient (0–80%) as eluant. Yield (Compound 2): 17.1 g (90%). Analysis: ES-MS (in MeOH): 633.1([M–H]$^-$, calculated:633.27)

EXAMPLE 3

Synthesis of monomer M1: 2,2'-bis(4-methacryloxyethoxy-3-methyl-5-methylamine-N,N'-diacetic acid-phenyl)propane (Compound 3)

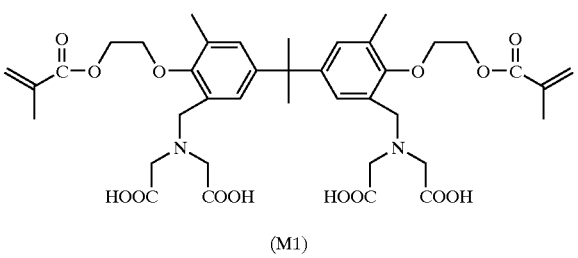

Compound 3

(M1)

To a solution of Compound 2 (12.68 g, 0.02 mol) in dry DMF (50 ml) was added 20.5 ml of triethylamine (0.15 mol). Then 5.2 g methacryloyl chloride (0.05 mol) was added dropwise to the stirred mixture at room temperature over one hour. After stirring overnight, 10% HCl was added to the mixture to pH 2.0, 500 ml acetone was added, and the precipitate was filtered off. The solvent was removed; and the monomer M1, Compound 3, was obtained from a silica gel column using $CH_2Cl_2$ with a MeOH gradient (0–70%) as eluant. Yield: 10.8 g (70%). Analysis:

$^1$H NMR ($CD_3OD$, 500 MHz) δ: 1.549 [s, 6H, $Ar_2$—C—($CH_3)_2$], 1.904 [s, 6H, 2 $CH2=C-CH_3$], 2.155 [s, 6H, 2 Ar—$CH_3$], 3.364 [s, 8H, 2 —N($CH_2CO_2H)_2$], 3.841 [s, 4H, 2 Ar—$CH_2$—N], 4.051 [t, 4H, 2 —O—$CH_2CH_2$—O—], 4.366 [t, 4H, 2 —O—$CH_2CH_2$—O—], 5.702 [s, 2H, 2 H—C=C—COO (trans)], 6.073 [s, 2H, 2 H—C=C—COO (cis)], 6.887 [s, 2H, 2 Ar—H(2)], 7.134 [s, 2H, 2 Ar—H (6)]. $^{13}$C NMR ($CD_3OD$, 500 MHz): 15.971 [Ar—$C$H$_3$], 18.059 [CH2=C—$C_3$], 30.556 [$Ar_2$—C($CH_3)_2$], 41.452 [$Ar_2$—$C$($CH_3)_2$], 51.976 [N—$CH_2CO_2H$], 53.761 [$CH_2$—N—$CH_2CO_2H$], 64.108 [Ar—O$CH_2$$CH_2$O—CO—], 70.502 [Ar—O$CH_2CH_2$O—CO—], 135.798[$CH_2=C$—$CH_3$], 166.610 [$CH_2=C(CH_3)COO$], 172.432 [N($CH_2CO_2H)_2$]. ES-MS (in MeOH): 769.2 ([M-H]$^-$, calculated: 769.33)

The $^1$H NMR, 13C NMR, and ES-MS data confirmed the expected structure of monomer M1.

EXAMPLE 4

Synthesis of the fluoride-releasing monomers M1-ZrF and M1-$Zr_2F_5$: 2,2'-bis(4-methacryloxyethoxy-3-methyl-5-methylamine-N,N'-diacetic acid-phenyl)propane complexes with zirconium and fluoride (Complexes 4, 5)

Complex 4

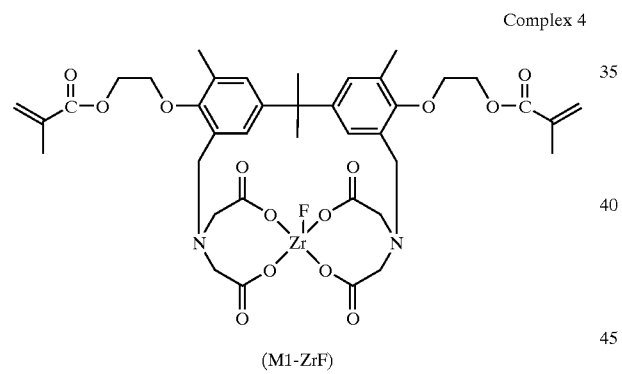

(M1-ZrF)

Complex 5

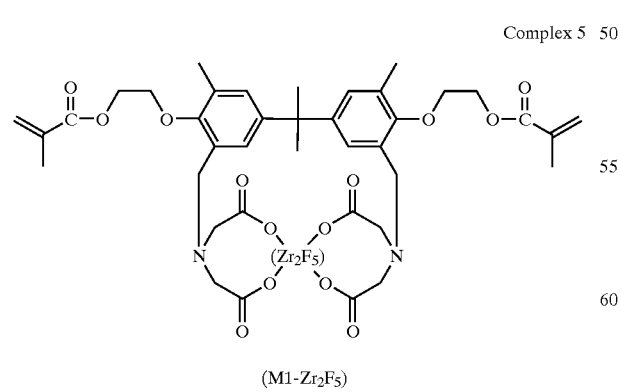

(M1-$Zr_2F_5$)

To a solution of 4.42 g (0.02 mol) of zirconium (IV) fluoride hydrate in 20 ml MeOH and 5 ml 48% aqueous HF, 7.70 g monomer M1 (Compound 3, 0.01 mol) in 50 ml MeOH was added under stirring at room temperature. After one hour of stirring, the solvent was removed under vacuum at 35° C. The mixture was dissolved in 2-propanol, and the solid was filtered off. The solvent was evaporated from the 2-propanol solution to obtain a mixture of Complexes 4 and 5 as white solids. Analysis: ES-MS (in MeOH): 875.4 ([M–4H+Zr+F]$^-$, calculated: 875.20), 1041.2 ([M–4H+2Zr+5F]–, theoretical value=1041.10). $^{19}$F NMR δ: 27.437, 28.374, 30.616. The 30.616 $^{19}$F NMR shift was attributed to the F in an M1-ZrF chelate, while the two slightly different shifts (27.437 and 28.374) indicated different F environments in M1-$Zr_2F_5$, such as terminal and bridge fluoride positions. The ES-MS and $^{19}$F NMR data confirmed the structures of the fluoride-releasing monomers M1-ZrF and M1-$Zr_2F_5$.

EXAMPLE 5

Synthesis of {[4,4-Bis-(4-hydroxyphenyl)-pentanoyl]-ethoxycarbonyl-methylamino}-acetic acid ethyl ester (Compound 6)

Compound 6

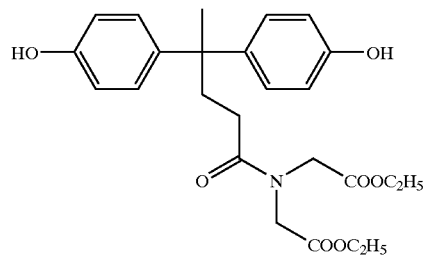

To a stirred suspension of 1-methyl-2-chloropyridiniumiodide (6.13 g, 24 mmol) in 1,4-dioxane (130 ml) were added 4,4-bis-(4-hydroxyphenyl)-pentanoic acid (5.73 g, 20 mmol) and triethylamine (4.86 g, 48 mmol) at room temperature. After dropwise addition of a solution of iminodiacetic acetate (4.92 g, 26 mmol) in 1,4-dioxane (50 ml), the mixture was stirred for about 10–20 min at 70° C. and monitored by ES-MS or TLC. The mixture was filtered, and the 1,4-dioxane was evaporated. The solid product was dissolved in dichloromethane (100 ml), and the solution was washed with 0.5 N aqueous HCl (4×100 ml) and brine (3×100 ml). The collected organic layer was evaporated and dried over sodium sulfate. The resulting product was further purified by flash chromatography by elution with dichloromethane:diethyl ether (40:1, v/v) to give a white solid. Yield: 5.13 g (56%). Analysis: IR ($CHCl_3$): ṽ(cm$^{-1}$)=3511.3, 1750.2, 1662.9, 1617.8 (m), 1593.3 (w), 1513.1 (ms), 874.8(ss), 613.4(s)

$^1$H-NMR (DMSO-$d_6$+CDCl$_3$): δ6.92, 6.63 (d, d, J=7.6, 7.6 Hz, 8H, ArH), 4.11–4.00 (m, 8H, CH$_2$), 2.21, 1.96 (t, t, J=7.6, 7.6 Hz, 4H, CH$_2$CH$_2$CON), 1.47 (s, CH$_3$), 1.22–1.16 (m, 2CH$_3$) $^{13}$C-NMR (DMSO-$d_6$+CDCl$_3$): δ173.38 (C=O, CON), 168.91 (C=O, 2COOH), 155.01, 139.33, 127.65, 114.60 (12ArC), 60.88, 60.39 (2CONCH$_2$), 49.88, 48.19 (2COOCH$_2$), 43.87 (CH$_2$CON), 36.69 (CH$_2$CH$_2$CON), 28.19 (t-C), 27.31 (CH$_3$), 14.0, 13.93 (2CH$_3$) ES-MS (MeOH): 456.3 (100, [M−H]$^−$, calculated: 456.21), 913.0 (3.7, [2M−H]$^−$), 480.4 (100, [M+Na]$^+$, calculated: 480.20).

EXAMPLE 6

Synthesis of {[4,4-Bis-(4-hydroxyphenyl)-pentanoyl]-hydroxycarbonyl-methylamino}-acetic acid (Compound 7)

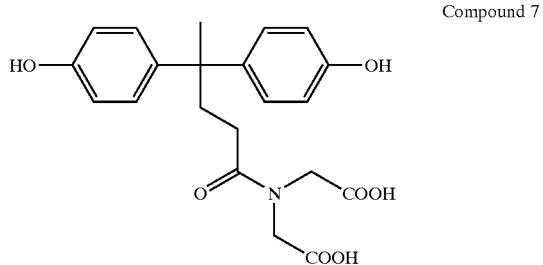

Compound 7

Synthesized compound 6 (2.29 g, 5 mmol) was added to 0.5 N aqueous NaOH (50 ml) and stirred for 5–10 minutes at room temperature. The solution was acidified to pH 1–2 by dropwise addition of concentrated HCl, and was then extracted with ethyl acetate (4×50 ml). The organic layer was dried over sodium sulfate and evaporated. The residue was then purified by flash chromatography by elution with dichloromethane:diethyl ether (40:1, v/v) to give a colorless oil. Yield: 1.77 g (88%). Analysis: IR (neat): $\tilde{v}$(cm$^{-1}$)=3406.6 (s, br), 1729.7 (s), 1655.0 (s), 1510.8 (s), 836.7(s), 670.7(m)

$^1$H-NMR (DMSO-$d_6$): δ6.93, 6.65 (d, d, J=8.0, 8.5 Hz, 8H, ArH), 3.99–3.93 (m, 8H, CH$_2$), 2.19, 1.98 (t, t, J=7.75, 8.05 Hz, 4H, CH$_2$CH$_2$CON), 1.47 (s, CH$_3$) $^{13}$C-NMR (DMSO-$d_6$): δ173.29 (C=O, CON), 171.24, 171.01 (C=O, 2COOH), 155.02, 139.58, 127.80, 114.76 (12ArC), 43.81 (CH$_2$CON), 36.76 (CH$_2$CH$_2$CON), 28.10 (t-C), 27.21 (CH$_3$) ES-MS (MeOH): 400.2 (100, [M−H]$^−$, calculated: 400.15), 424.4 (100, [M+Na]$^+$, calculated: 424.15).

EXAMPLE 7

Synthesis of monomer M2: 2-Methacrylic acid 3-[4-(3-(bis-carboxymethyl-carbamoyl)-1-{4-[2-hydroxy-3-(2-methacryloyloxy)-propoxy]-phenyl}-1-methyl-propyl)-phenoxy]-2-hydroxy-propyl ester (Compound 8)

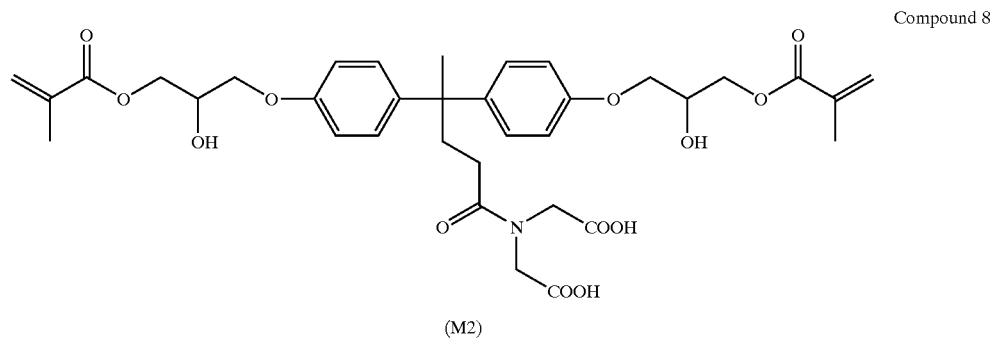

Compound 8

(M2)

A mixture of Compound 7 (11.09 g, 27.6 mmol) and 2,3-epoxypropyl methacrylate (28.30 g, 199 mmol) in anhydrous 1,4-dioxane (60 ml) were stirred under nitrogen for 25 h at 100° C., and monitored by TLC and ES-MS. The solvent was evaporated, and the residue was purified by flash chromatography by elution with dichloromethane:ethyl acetate (5:1, v/v) to give a white glassy solid. Yield: 13.64 g (72%). Analysis: IR (dioxane): $\tilde{v}$(cm$^{-1}$)=3373.8 (s, br), 1750.4 (s), 1716.3 (ss), 1637.7 (s), 1613.6 (m,), 1596.6 (m), 1514.6(s), 838.1 (s), 656.9 (m)

$^1$H-NMR (DMSO-$d_6$+CDCl$_3$): δ6.91, 6.63 (d, d, J=8.4, 8.8 Hz, 8H, ArH), 6.07, 5.59 (s, d, J=1.6, 4H, 2CH$_2$=), 3.96–4.2, 3.61–3.53 (m, m,14H, 2CH and 6CH$_2$), 2.26–2.18, 2.02–1.97 (m, m, 4H, CH$_2$CH$_2$CON), 1.89 (s, 6H, CH$_3$—C=CH$_2$), 1.46 (s, CH$_3$) $^{13}$C-NMR (DMSO-$d_6$+CD$^{13}$C):

δ173.49 (C=O, CON), 168.94, 168.91 (C=O, 2COOH), 166.38 (C=O, $CH_2$=C$\underline{C}$=O), 154.99, 139.41, 127.70, 114.65 (12ArC), 135.76 (C=), 125.68 ($CH_2$=), 67.22, 67.19 (2CH—OH), 66.25, 65.73, 65.43, 65.06 (4$CH_2$), 59.66, 59.59 (2CON$\underline{C}H_2$), 49.74, 48.03 (2COO$\underline{C}H_2$), 43.90 ($CH_2$CON), 36.71 ($\underline{C}H_2CH_2$CON), 28.18 (t-C), 27.28 ($CH_3$), 18.06, 17.99 (2$CH_3$—C=$CH_2$) ES-MS (MeOH): 684.4 (100, $[M-H]^-$, calculated: 684.27), 708.6 (100, $[M+Na]^+$, calculated: 708.27).

The FT-IR, NMR, and ESMS data confirmed the structure of monomer M2.

EXAMPLE 8

Preparation of fluoride-releasing monomer: M2-$ZrF_2$ (Complex 9)

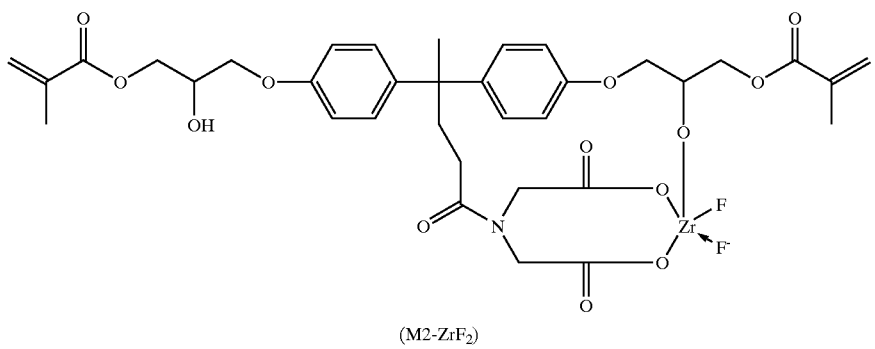

(M2-$ZrF_2$)

Zirconium (IV) fluoride hydrate (0.845 g, 3.82 mmol) was dissolved in methanol (3 ml) in the presence of concentrated HF (48%, 1.25 ml), The resulting solution was mixed with a solution of monomer M2 (Compound 8, 2.62 g, 3.82 mmol) in methanol (10 ml) to form a zirconium (IV)-fluoride complex of M2. After the solvent was evaporated over $Ca(OH)_2$ under vacuum, the residue was redissolved in isopropanol (200 ml). The solvent was evaporated and the residue was dried in vacuo to give a nearly white solid (2.30 g, 74%). Analysis: IR ($CH_3OH$): $\tilde{v}(cm^{-1})$=1748.3 (s), 1717.3 (s), 1639.6 (s), 1614.6 (m), 1512.0 (s), 831.4 (s), 768.1 (s), 728.0 (s)

$^1$H-NMR ($CD_3OD$+DMSO-$d_6$): δ7.00, 6.72 (d, d, J=9.0, 8.5 Hz, 8H, ArH), 6.13, 5.66 (s, d, J=2.25, 4H, 2$CH_2$=), 4.22–3.52 (m, 14H, 2CH and 6$CH_2$), 2.30–2.27, 2.09–2.04 (t, m, 4H, $CH_2CH_2$CON), 1.94 (s, 6H, $CH_3$—C=$CH_2$), 1.52 (s, $CH_3$) $^{13}$C-NMR ($CD_3OD$+DMSO-$d_6$): δ176.63 (C=O, CON), 171.42, 171.23 (C=O, 2COOH), 168.77 (C=O, $CH_2$=C$\underline{C}$=O), 156.20, 141.37, 129.31, 115.95 (12ArC), 137.49 (C=), 126.86 ($CH_2$), 73.80 (2CH—OH), 71.02, 66.91, 64.32, 64.01 (4$CH_2$), 61.59 (2CON$CH_2$), 51.27, 49.77 (2COO$\underline{C}H_2$), 45.49 ($\underline{C}H_2$CON), 38.15 ($CH_2CH_2$CON), 29.80 (t-C), 28.18 ($CH_3$), 18.69 (2$CH_3$—C=$CH_2$) ES-MS (MeOH): 810.4 (100, $[M-3H+Zr+2F]^-$, calculated: 810.15).

The FT-IR, NMR, and ESMS data confirmed the structure of fluoride-releasing monomer: M2-$ZrF_2$.

EXAMPLES 9 and 10
Preparation of Experimental Composites

Unfilled activated resin (Lot No. 12166-KG13), silanized filler (Lot No. 12204-JE39), and Synergy Flow™ manual and syringe non-fluoride-releasing restorative composites were provided by Coltène Whaledent (Mahwah, N.J.). Tetric-Flow™ fluoride-releasing restorative composite was obtained from Ivoclar Vivadent (Amherst, N.Y.). Flows-Rite™ restorative composite was obtained from Pulpdent (Watertown, Mass.). Two experimental composites were fabricated by manually mixing 70% unfilled activated resin and 30% of either: (1) a mixture of the synthesized monomers M1-ZrF and M1-$Zr_2F_5$ (Experimental Composite 1), or (2) the synthesized monomer M2-$ZrF_2$ (Experimental Composite 2). The silanized filler was hand-mixed with the matrix monomer(s), and with commercially-obtained initiators (0.05% camphorquinone/0.05% phenyl-propanedione/0.3% 2-(dimethylamino)ethyl methacrylate). The filler load was 54 wt %. In the final composite, the content of the novel fluoride-zirconium-monomer complex was about 12% by weight. For mechanical tests, Synergy Flow™ (manual) was prepared by manually mixing unfilled activated resin with 54 weight % silanized filler.

EXAMPLES 11 and 12

Fluoride Release and Recharge

The two experimental fluoride-releasing flowable composites of Examples 9 and 10, and the three commercial flowable composites Synergy Flow™, Tetric Flow™, and Flow-Rite™ were tested to evaluate their respective fluoride release and fluoride recharge capabilities. Cylindrical specimens 4 mm diameter×9 mm length (n=5) were prepared from each composite, and were light-cured using a Virtuoso™ curing light (Den-Mat) for 18 s on each surface and on each longitudinal side. The specimens were then stored in 3 ml deionized water. Fluoride concentrations were measured daily for 14 days using an ion-selective electrode (Thermo-Orion). After each measurement, the storage solution was replaced with pure deionized water. The specimens were then recharged with fluoride by applying 60 Second Taste™ Gel (Pascal Co., Bellevue, Wash.)—an acidulated phosphate fluoride (APF) topical agent (1.23% $F^-$, pH=3.5)—for one minute, followed by rinsing in deionized water for one minute. Fluoride release from the recharged samples was measured daily for four days, with the storage solution replaced daily by deionized water. The data were analyzed by ANOVA.

As shown in Table 1, the experimental materials had significantly and substantially higher fluoride-release and fluoride-recharge capabilities than did the commercial materials (P<0.05). The measurements are given in $\mu g/cm^2$, referring to the amount of fluoride released per unit surface area of the composite.

TABLE 1

Fluoride release and recharge of the experimental and commercial composites.

| Material | Cumulative 14-day F⁻ release ($\mu$g/cm$^2$) ± SD | Cumulative F⁻ release over 3 days after recharge ($\mu$g/cm$^2$) ± SD |
|---|---|---|
| Experimental Composite 1 | 27.94 ± 3.10 | 14.07 ± 2.42 |
| Experimental Composite 2 | 25.63 ± 12.14 | 33.51 ± 5.62 |
| Synergy Flow ™ (Non-F⁻-releasing) | Not Detected | 5.40 ± 1.09 |
| Tetric Flow ™ (F⁻-releasing) | 0.98 ± 0.22 | 11.658 ± 1.70 |
| Flow-Rite ™ (F⁻-releasing) | 1.30 ± 0.51 | 5.69 ± 1.97 |

EXAMPLES 13 and 14

Mechanical Properties Tests

Cylindrical specimens 4 mm diameter×9 mm length (n=10) were prepared for compression tests, and rectangular specimens 2 mm×2 mm×25 mm (n=10) were prepared for flexure strength tests. Compressive strength and flexure strength tests were conducted 24 hours after sample preparation on an Instron 4411 universal test machine with a crosshead speed of 1 mm/min. The results are shown in Table 2. The data were analyzed by ANOVA. The mechanical properties of the experimental materials were generally comparable to, albeit somewhat lower than, those of the commercial materials. For comparison, the ANSI/ADA standard for flexure strength of dental composites is 50 MPa. (There is currently no ANSI/ADA standard for compressive strength.)

TABLE 2

Mechanical properties of the experimental and commercial composites

| Material | Compressive Strength (MPa) ± SD | Flexure Strength (MPa) ± SD |
|---|---|---|
| Experimental Composite 1 | 197.2 ± 41.0 | 55.4 ± 7.0 |
| Experimental Composite 2 | 157.0 ± 11.43 | 62.8 ± 5.7 |
| Synergy Flow ™ (syringe) | 297.2 ± 24.3 | 96.0 ± 20.2 |
| Synergy Flow ™ (manual) | 202.5 ± 22.7 | 67.8 ± 10.5 |
| Tetric Flow ™ | 261.0 ± 25.9 | 82.6 ± 7.0 |
| Flow-Rite ™ | 213.1 ± 23.6 | 85.7 ± 3.6 |

EXAMPLES 15–18

Water Sorption and Solubility Tests

Water sorption and solubility tests were conducted according to ANSI/ADA Specification No. 27 (1993). The water sorption of Experimental Composite 1 was significantly higher than that of the commercial materials, but still within the ANSI/ADA specifications (50 $\mu$g/mm$^3$). The water sorption of Experimental Composite 2 was similar to that of the commercial materials. The water solubilities of the Experimental Composites were similar to those of the commercial materials, and were within the ANSI/ADA specifications (50 $\mu$g/mm$^3$) (negative values indicating permanently absorbed water).

TABLE 3

Water sorption and solubility of the experimental and commercial composites.

| | Experimental Composite 1 | Experimental Composite 2 | Synergy Flow ™ | Tetric Flow ™ |
|---|---|---|---|---|
| Water sorption ($\mu$g/mm$^3$) | 47.14 ± 3.45 | 13.28 ± 7.13 | 17.34 ± 1.17 | 16.04 ± 2.12 |
| Solubility ($\mu$g/mm$^3$) | −0.10 ± 3.83 | 1.27 ± 0.87 | 2.02 ± 1.46 | 4.74 ± 2.56 |

In summary, the preliminary results given in the Examples above demonstrated that the novel fluoride-releasing monomers enhanced fluoride release and recharge in dental restorative materials, even in the absence of traditional fluoride-releasing fillers. It should be the case that fluoride release will increase further if fluoride-releasing fillers were used in conjunction with the novel fluoride-releasing monomers. The hand-mixing process used to prepare the Experimental Composites is known generally to produce materials with poorer mechanical properties than those prepared with industrial composite blenders such as are known in the art, but that were not immediately available when these prototype experiments were conducted. For example, as shown in Table 2, the Synergy Flow™ (syringe) material, which is commercial sold, had significantly higher mechanical properties (ca. 30%) than the Synergy Flow™ (manual) material, which had the same composition but was mixed manually. It is therefore expected that the mechanical properties of dental materials made with the novel fluoride-releasing monomers will improve when fabricated using composite blenders known in the art. Further improvements in mechanical properties are expected to result from optimizing the photoinitiation system through techniques known in the art, for example, the amounts and ratios of photoinitiator, accelerator, additives such as diphenyl-iodonium hexafluorophosphate, and the like.

The complete disclosures of all references cited in this specification are hereby incorporated by reference. Also incorporated by reference are the entire texts of the following, which are not believed to be prior art to the present application: X. Ding et al., "Mechanical Properties of Experimental Fluoride-Releasing Dental Composites," Paper #1316 to be presented at the 32$^{nd}$ Annual Meeting of the American Association of Dental Research and 27$^{th}$ Annual Meeting of the Canadian Association for Dental Research (Mar. 12–15, 2003, San Antonio, Tex.); X. Xu et al., "Fluoride Release and Recharge of Experimental Dental Composites Containing Fluoride-Exchanging Metal Chelates," Paper #0936 to be presented at the 32$^{nd}$ Annual Meeting of the American Association of Dental Research and 27$^{th}$ Annual Meeting of the Canadian Association for Dental Research (Mar. 12–15, 2003, San Antonio, Tex.); X. Ding et al., "Effects of Silane Coupling Agents on the Fluoride Release from Experimental Dental Composite," Abst. #1970, p. A-255, *Journal of Dental Research*, vol. 81 (Special Issue A) (80$^{th}$ General Meeting of International Association for Dental Research, 31$_{st}$ Annual Meeting of the American Association of Dental Research, and 26$^{th}$ Annual Meeting of the Canadian Association for Dental Research, Mar. 6–9, 2002, San Diego, Calif.); and J. Burgess et al., "Novel Fluoride Releasing Dental Composite Resin," Research Grant Proposal submitted to Joe W. and Dorothy Dorsett Brown Foundation (1999).

What is claimed:

1. A compound selected from the group of compounds having one of the structures M1 to M20 as follows:

M1
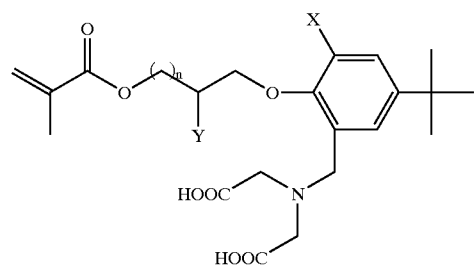
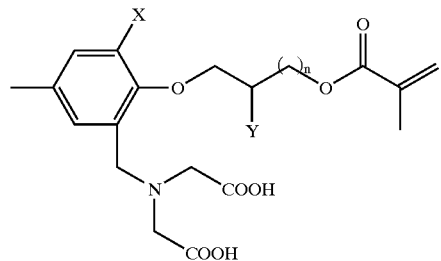
M2
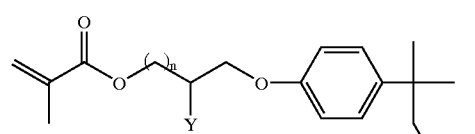
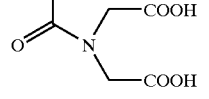
M3
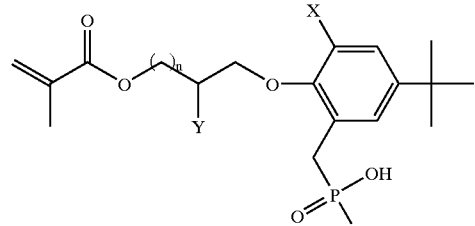
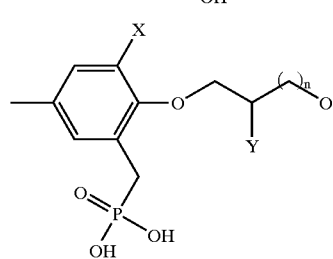
M4
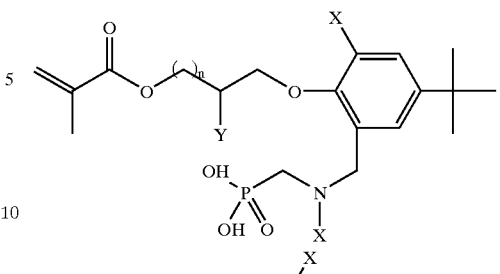
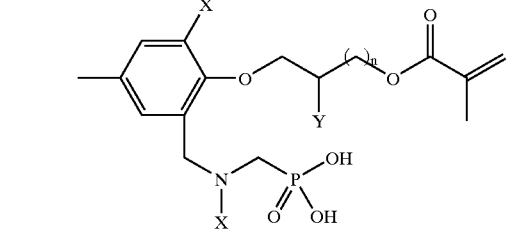
M5
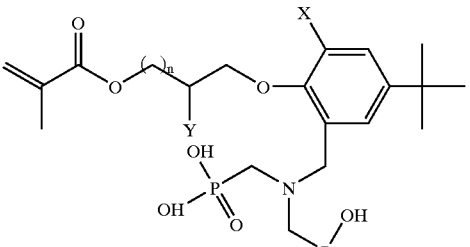
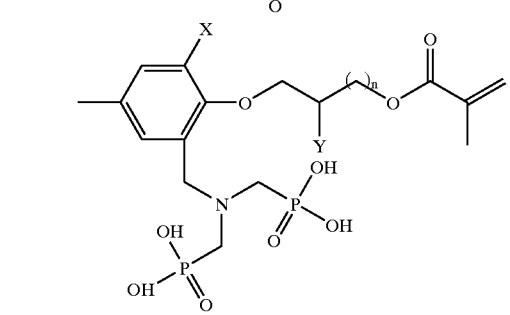
M6
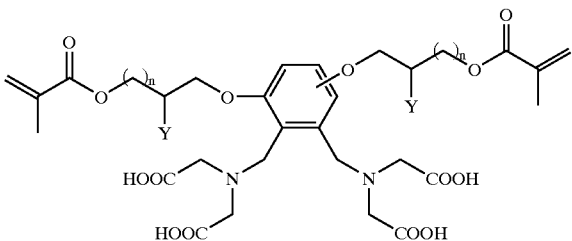
M7
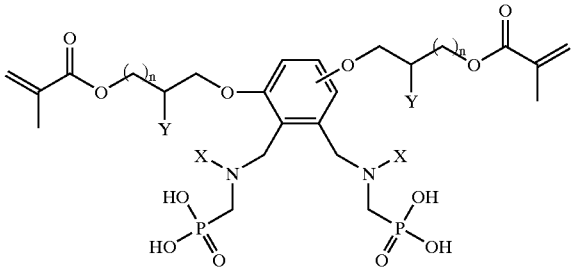

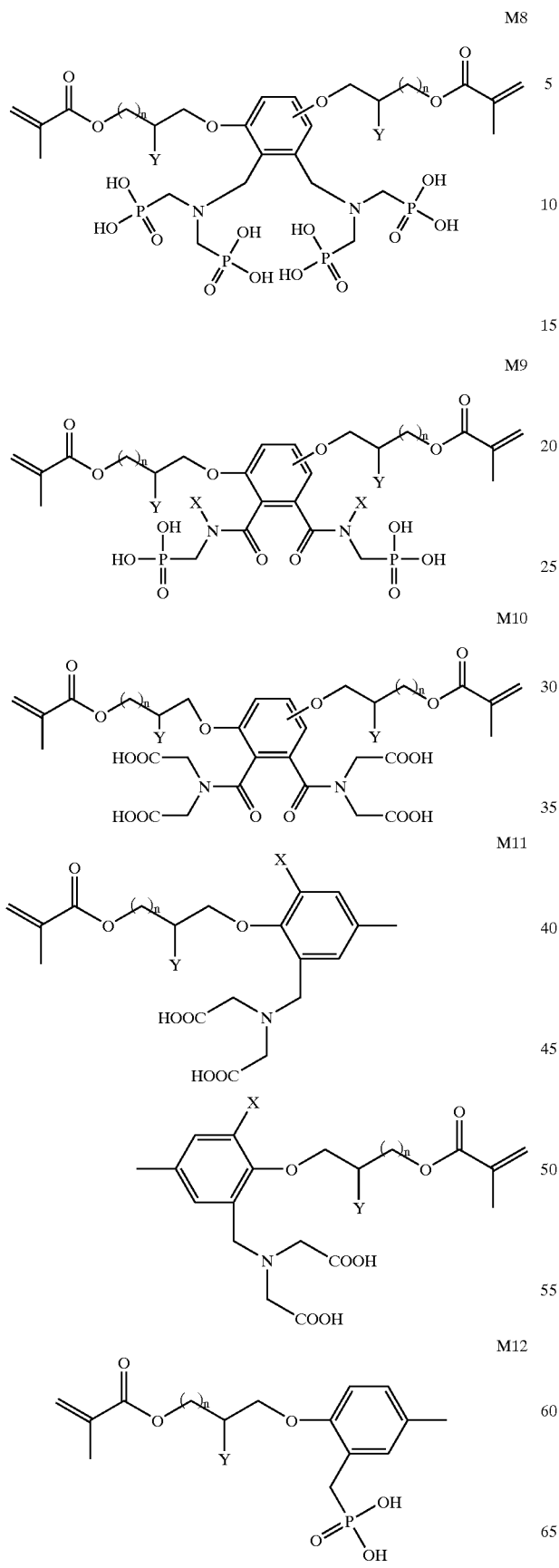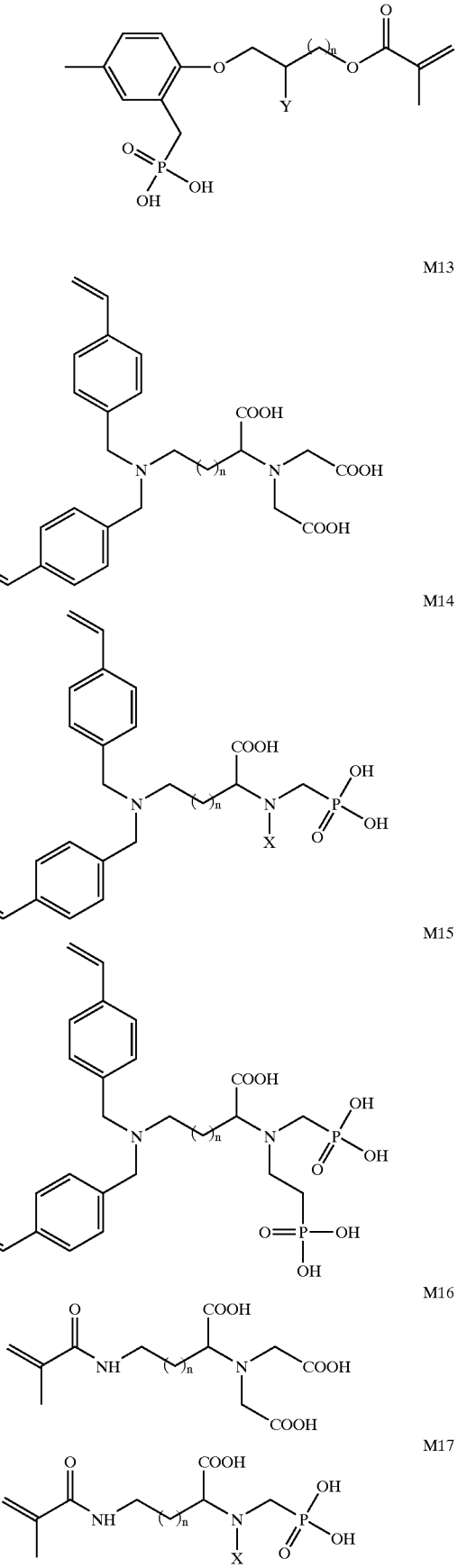

-continued

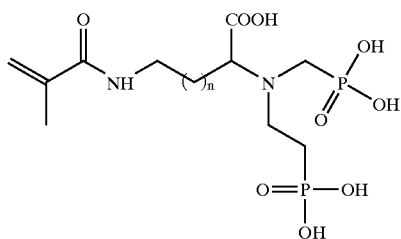

M18

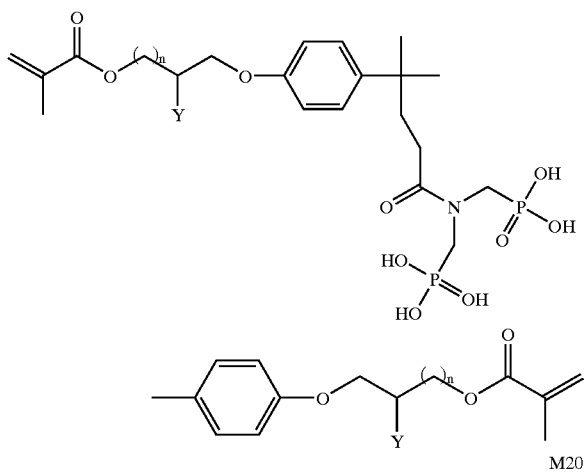

M19

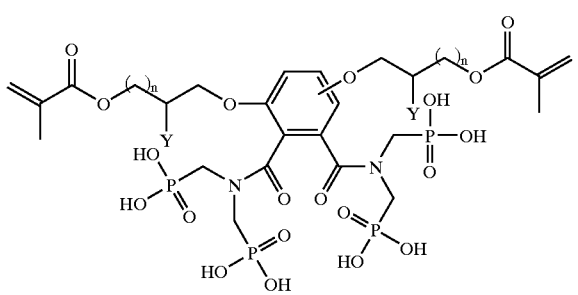

M20 wherein:

X denotes hydrogen, or a substituted or unsubstituted alkyl group having from 1 to 12 carbon atoms; and the various X moieties may be the same or different;

Y is selected from the group consisting of hydrogen, hydroxyl, an ester of a phosphoric acid, or a half ester of an aliphatic or aromatic diacid or triacid having from 2 to 12 carbon atoms; and the various Y moieties may be the same or different; and n is an integer from 0 to 12.

2. A complex comprising a compound as recited in claim 1; and one or more metal atoms or metal ions; wherein the compound is chelated to said one or more metal atoms or metal ions; and wherein said one or more metal atoms or metal ions are selected from the group consisting of Sn, Zn, Sr, Al, La, Sb, Yb, Ti, Zr, Ce, or Th.

3. A complex as recited in claim 2, wherein said one or more metal atoms or metal ions comprise $Zr^{+4}$.

4. A complex as recited in claim 3, additionally comprising one or more fluoride ions coordinated to said $Zr^{+4}$.

5. A complex as recited in claim 2, additionally comprising one or more fluoride ions coordinated to said metal atoms or metal ions.

6. A compound as recited in claim 1, wherein Y is a diacid or triacid selected from the group consisting of oxalic acid, malonic acid, maleic acid, a disubstituted maleic acid, succinic acid, fumaric acid, malic acid, tartaric acid, glutaric acid, glutaconic acid, adipic acid, pimelic acid, cyclohexen-1,2-diacid, (o, m, or p)-phthalic acid, citric acid, hydroxyphthalic acid, suberic acid, trimellitic acid, sebaric acid; or wherein Y is a salt of such a diacid or triacid.

* * * * *